United States Patent [19]

Bar-On et al.

[11] Patent Number: 5,122,533
[45] Date of Patent: Jun. 16, 1992

[54] TOPICAL PHARMACEUTICAL COMPOSITIONS

[76] Inventors: Ernest Bar-On, P.O. Box 39008, Tel-Aviv; Sophia L. Segal, P.O. Box 257, Givatayim; Anatol Krakowski, 24a Dubnov Street, Tel-Aviv, all of Israel

[21] Appl. No.: 630,207

[22] Filed: Dec. 19, 1990

[30] Foreign Application Priority Data

Jun. 20, 1990 [IL] Israel ......................................... 94806

[51] Int. Cl.⁵ ..................... A61K 31/19; A61K 31/415
[52] U.S. Cl. .................................... 514/390; 514/557; 514/863
[58] Field of Search ...................... 514/557, 390, 863

[56] References Cited

U.S. PATENT DOCUMENTS 3,514,515  5/1970  Woolf ................................. 424/317
4,627,934  12/1986  Lindauer et al. ................... 514/390

OTHER PUBLICATIONS

Chemical Abstracts 82:64494q, 1975 (I).
Chemical Abstracts 102:191157p, 1985 (II).

*Primary Examiner*—Leonard Schenkman
*Attorney, Agent, or Firm*—Oblon, Spivak, McClelland, Maier & Neustadt

[57] ABSTRACT

The invention relates to a pharmaceutical composition for removing necrotic skin tissue in mammals, including humans. The composition comprises in combination a substituted thiol in which the hydrogen sulfide moiety is substituted by an organic residue, alantoine, a physiologically acceptable alkaline substance, an application vehicle for the thiol and alkaline constituents, and water for activating the composition. Suitable application vehicles are body giving materials of an oily nature, emulsifiers and a thickening agent, with adequate water to provide the required consistency. Suitable thiols are thioglycolates and similar compounds.

13 Claims, No Drawings

TOPICAL PHARMACEUTICAL COMPOSITIONS

Compositions and method for treating the parakeratotic skin layer formed by a variety of dermatological diseases especially psoriasis is provided. The scaly layers of necrotic tissue are treated with a preparation comprising a substituted thiol allantoin base, water and an application vehicle. A number of suitable preparations are illustrated.

FIELD OF THE INVENTION

The invention relates to pharmaceutical compositions for the treatment of humans having necrotic skin tissue and more particularly to compositions for the treatment of psoriasis. Parakeratotic layers of skin in the affected areas are removed by a preparation comprising a substituted thiol allantoin, water, an alkaline substance, dispersed in a vehicle which provides protection to the underlying psoriasis lesion.

BACKGROUND OF THE INVENTION

Psoriasis is a chronic, recurrent, papulosquamous dermatosis, the distinctive lesion being a silvery-grey scaling papule or plaque.

The symptoms of psoriasis are small, flat-topped papules (pimples), which develop into larger plaques, which plaques are dull-red in color, covered and surmounted by fine silvery scales. These scales can become thick parakeratotic horny layers which are very difficult to remove. Upon scraping, the scales can be removed to a certain extent, and a red shining surface appears. These primary afflictions usually occur on the knees, elbows, scalp, hairline, nails, back and neck, although no part of the body is immune. The lesions of psoriasis tend to connect with each other. The skin disorder is chronic; and as yet incurable.

Medical science has not been able to cure psoriasis, but several methods of treatment are known to ease the suffering caused by the disease for a short period of time. These methods generally involve the removal of scales by applying formulations that soften them followed by further treatment of the newly-exposed lesion areas. One such method for the removal of the scales is the application of salicylic acid for periods of up to 48 hours. This is time consuming and dangerous in that salicylic acid, which has toxic properties, is absorbed through the skin. The descaled area is then treated with any of a large number of compounds including tars, corticosteroids and the like to heal the underlying psoriasis lesion.

SUMMARY OF THE INVENTION

The invention provides compositions for the treatment of mammals having necrotic skin tissue and especially for the treatment of Psoriasis in humans.

It is also an object to provide a method for removing the parakeratotic layers which form on psoriasis lesions while protecting and treating the underlying lesions. The compositions comprise a substituted thiol in which the hydrogen sulfide is substituted by an organic residue, allantoin, an alkaline substance, water and an application vehicle.

A further important constituent is allantoin which fulfills a variety of functions. It seems to interact with the thioglycolate forming an addition compound or complex. The allantoin serves as cleaning agent for necrotic tissue and for scaly tissue, while protecting the underlying tissues from any harm or damage by other constituents of the preparation. The allantoin results in a soothing action and helps to restore normal function of the epidermic and enhances healing. It further enhances healthy granulation and epithalization. It is believed that the interaction of the allantoin with the thioglycolate prevents any adverse skin reaction due to this component and due to the alkaline components. The allantoin is used in a wide range of concentrations, and generally in the range of from about 0.5 weight-% of the composition. It is clear that a higher content can be used, and that allantoin can also come instead of part of the dispersing agent.

The preparations remain in contact with the parakeratotic layer for at least 10 minutes, sometimes up to 30 minutes; and the preparation and parakeratotic layers are removed from the affected area.

The preparations which are useful contain as the active agent about 2 to 15 percent by weight, based on the final composition, of a substituted thiol in which the hydrogen atom in hydrogen sulfide is substituted by an organic residue, such as a thioglycolate: The most effective and least odoriferous are the guanidine, ethylene diamine, alkali and alkaline earth metal salts of thioglycollic acid and thiolactic acid.

The preparations also contain an alkaline substance in sufficient amount to provide a pH of 10.5 to 12.5, preferably 11 to 12, in the final composition. A higher pH reduces treatment time but may tend to cause irritation. Preferably a solid basic material such as guanadine, alkali and alkaline earth metal hydroxides, carbonates, silicates, and tribasic phosphates. The basic material will ordinarily comprise from 4 to 12 per cent of the final preparation.

The foregoing three essential constituents of the preparation are intimately dispersed in an application vehicle and protects the underlying lesion from undue irritation.

The allantoin and the application vehicle have emollient properties to aid in softening the parakeratotic layer and to permit the removal of this layer without undue irritation to the underlying lesion. Preferably the application vehicle is an emulsion since the thiol and the basic material require water to achieve their full activity. Also the application vehicle, except for its water content, is non-reactive with the two essential constituents of the preparation. The application vehicle advantageously has a viscosity of about 1000 to 5000 centipoises. Desirably the vehicle will be relatively non-drying.

The foregoing properties of the application vehicle are satisfied by a large number of application vehicles well-known in the art. The vehicles which can be used whether characterized as creams, pastes, aqueous gels, slurries, ointments, emulsions, mucilaginous carriers, jellies or liquids, are in general "constructed" from a variety of materials each of which provide the mixture with one or more of the necessary properties. Each of these materials can be grouped in one of three categories in accordance with its function in the preparation although in some instances a particular material may have a dual function. The materials by category are: (1) a body-giving substance; (2) an emulsifier to emulsify the lipophilic substance in water; and (3) a thickening material to thicken the oil-in-water type emulsion produced by interaction of (1) and (2) to suspend any undissolved portions of solid basic material and substituted thiol.

Body and good emollient properties are obtained by a water-alcohol emulsion, the alcohols being for example, cetyl, stearyl, lauryl or oleyl alcohol. Less emolliency but excellent body is achieved with water-vegetable or water-synthetic gum emulsions. Also suitable are esters such as isopropyl myristate and butyl stearate. These vehicle constituents are essentially neutral, i.e. non-reactive with the thiol and the alkaline substance, and provide a desirable cream-like consistency to the preparation. A like consistency but lesser emollient property is obtained by agents such as tragacanth, karaya, guar, and quince seed extracts or synthetic materials such as sodium dodecyl xanthate, methyl or hydroxyethyl cellulose or other water dispersible non-acidic cellulose ethers, sodium cellulose glycolate, water-dispersible polyvinyl alcohols, polyvinylpyrrolidone or chemically modified starches and sugars.

Another class of body-giving substances which have excellent lipophilic and emollient properties are sterols of animal and vegetable origin. These include $C_{27}$–$C_{29}$ compounds such as cholesterol, 7-dehydrocholesterol, ergosterol, ergostanol. Preferably, the sterol is unsaponifiable lanolin fraction of commerce containing principally lanolin alcohols. These are available commercially as "Cerelan", "Amerchol", "Hartolan" and "Dusoran 60". The unsaponifiable lanolin fraction can be in solid or semi-solid form.

A particularly useful body-giving substance providing good emollient properties is a monoamide of a lower alkanolamine, having primary and secondary amino groups and only lower alkyl and lower hydroxyalkyl substituents, and a $C_6$ to $C_{22}$ monocarboxylic fatty acid. $C_6$ to $C_{22}$ monocarboxylic acids used to form the monoamides are the usual saturated and unsaturated fatty acids of commerce and include caprylicacid, lauric acid, myristic acid, palmitic acid, stearic acid, oleic acid, palmitoleic acid, linoleic acid, linolenic acid and natural and synthetic admixtures of these acids, such as coconut oil fatty acids and soybean oil fatty acids. The alkanolamines used to form the monoamides are the lower alkanolamines having a primary or secondary amino group.

The monoamides described above are prepared by heating approximately equal molar proportions of the fatty acid and the alkanolamine to a temperature in the range of about 140° to 180° C. and distilling off the water formed in the condensation.

Other body-giving substances such as natural and synthetic waxes, semi-solid and solid hydrocarbons, petrolatum, paraffin wax, microcristalline wax, spermaceti, beeswax, ceresin, lecithin, cephalin and hydrogenated vegetable oils can be used.

According to a preferred embodiment of the invention, the compositions comprise (by weight) about 2.0 to 12 percent alkaline earth thioglycolate, 2 to 5 per cent allantoin, 5 to 15 percent alkaline earth or alkali metal hydroxide or a combination of hydroxide and carbonate, water and a suitable emmolient base. The compositions optionally contain one or more of antioxidant, preservative, soothing agent, fragrance and coloring agent.

The alkaline substance of choice is calcium hydroxide; the substituted thiol of choice is calcium thioglycolate; a preferred antioxidant is sodium sulfite, a preferred preservative is Nipagin; a preferred soothing agent is allantoin. A wide variety of emollient bases can be used.

The water continued in the composition acts as a "catalyst" and activates the interaction of the substituted thiol compound and the basic substance.

It is clear that emulsions are preferred, as these facilitate the combination of a variety of substances of the type used in the compositions of the invention.

The preparations can contain coloring matter, such as vegetable and synthetic dyes, perfumes such as musk, civet, ambergris and castor, sage, thyme, mint, cinnamon, cassia, cedar, sandal wood, rose, violet anise, caraway, and mixtures thereof. They can contain bacteriostats, such as bithionol, hexetidine, hexachlorophene and the like. They can contain sodium sulfite as an antioxidant, zinc oxide to reduce odor, solvents such as propylene glycol and glycerine to provide smoothness and homogeneity to the cream and glycerol to provide additional humectant properties.

In order to more clearly describe the invention the following representative preparations for the removal of necrotic tissue are given

| PREPARATION I | |
| --- | --- |
| | Weight-% |
| Calcium thioglycolate | 3.5 |
| Calcium hydroxide | 7.0 |
| Allantoin | 2.5 |
| Cetyl alcohol flakes | 4.5 |
| Sodium lauryl sulfate | 0.5 |
| Sodium silicate solution (42.5° Be) | 3.5 |
| Perfume | 0.5 |
| Distilled water | 78.0 |
| | 100.0 |

The above preparation is prepared as follows. (Basis 1000 grams of final preparation). Dissolve 0.9 gram of sodium lauryl sulfate in 155 ml of hot water (65° C.). Add the sodium silicate solution to the aqueous solution and mix thoroughly. Add melted cetyl alcohol and allantoin to this mixture while it is still hot; then agitate the mixture while cooling to form an emulsion. Add the emulsion already prepared to this slurry and agitate this admixture for 30 minutes at 40° C. In yet another vessel prepare a suspension by mixing the calcium hydroxide and calcium thioglycolate in 110 ml of distilled water containing 0.1 grams of sodium lauryl sulfate. Add this suspension to the previously prepared mixture of emulsion and then agitate at 40° C. Add perfume and continue agitation for 30 minutes. Add additional water if necessary to make the proper weight.

| PREPARATION II | |
| --- | --- |
| | Weight-% |
| Calcium thiolacetate | 5.0 |
| Allantoin | 1.2 |
| Calcium hydroxide | 10.8 |
| Colloidal clay | 15.0 |
| Perfume | 2.0 |
| Water | 66.0 |
| | 100.0 |

| PREPARATION III | |
| --- | --- |
| Calcium thioglycolate | 9.0 |
| Calcium hydroxide | 8.0 |
| Allantoin | 4.0 |
| Sodium dodecyl xanthate | 15.0 |
| Purified sperm oil | 5.0 |
| Water | 59.0 |
| | 100.0 |

| PREPARATION IV | |
|---|---|
| | Weight-% |
| Sodium thiolactate | 5.0 |
| Allantoin | 3.0 |
| Sodium stereate | 6.0 |
| Sodium carbonate | 20.0 |
| Sodium lauryl sulfate | 2.0 |
| Water | 64.0 |
| | 100.0 |

| PREPARATION V | |
|---|---|
| Methyl cellulose (4000 cps) | 2.5 |
| Potassium thioglycolate | 4.0 |
| Allantoin | 2.0 |
| Calcium hydroxide | 3.5 |
| Sorbitol | 5.0 |
| Water | 83.0 |
| | 100.0 |

| PREPARATION VI | |
|---|---|
| Hydroxyethyl cellulose | 3.0 |
| Sodium thiolactate | 6.0 |
| Calcium hydroxide | 4.0 |
| Maunitol | 6.0 |
| Allantoin | 0.5 |
| Water | 80.5 |
| | 100.0 |

| PREPARATION VII | |
|---|---|
| | Weight-% |
| Magnesium thiolactate | 10.0 |
| Magnesium hydroxide | 12.0 |
| Allantoin | 3.0 |
| Oleyl alcohol | 5.0 |
| Potassium oleyl sulfate | 1.0 |
| Sodium silicate | 13.0 |
| Distilled water | 56.0 |
| | 100.- |

| PREPARATION VIII | |
|---|---|
| Sodium thioglycolate | 15.0 |
| Calcium hydroxide | 12.5 |
| Sodium stearate | 11.0 |
| Allantoin | 6.0 |
| Polyglycol monostearate | 3.5 |
| Distilled water | 52.0 |
| | 100.0 |

A test has been made on 60 patients, 31 with psoriasis and 29 with normal skin, regarding the tolerance of the preparations by the skin. The test was as follows: A 5 mm heavy layer of cream was applied on the skin of the back and arm with circular motion. The cream was left on the skin 30 minutes which is twice the normal application, and then removed with warm water. The skin was checked for reaction after 30 minutes, after 24, and after 48 hours.

The cream was highly efficient in removing the scales due to psoriasis, leaving the underlying healthy tissue without any irritation (redness or swelling), nor was any toxic or allergic effect apparent.

EXAMPLE I

To the skin of 22 patients having a 2-3 mm layer, a composition of the preparation I was applied. A control was run with 20 healthy patients. The preparation was applied in circulatory motions on the skin of the back or an arm, in a layer of 2-3 mm thickness, on a surface of about 5 cm diameter, left on the skin for 30 minutes, and washed off with warm water. The scales were washed off simultaneously by the warm water bath. The skin was examined for reddening and swelling immediately after the preparation was removed, after 24 hours and after 48 hours. Scale removal was highly effective and no adverse effects were observed.

The test was repeated with groups of patients, using preparations II to VIII under similar conditions. Practically identical results were obtained.

We claim:

1. A method for removing necrotic tissue of patients afflicted by psoriasis which comprises applying to the affected skin a composition comprising:
   (1) about 2 to 15 percent by weight, based on the total composition, of a substituted thiol selected from the group consisting of the guanidine, ethylene diamine, alkali and alkaline earth metal salts of thioglycolic acid and thiolactic acid, and mixtures thereof;
   (2) 0.5 to 5 percent by weight allantoin;
   (3) an alkaline substance in sufficient amount to provide a pH of 10.5 to 12.5 in the final preparation;
   (4) an application vehicle for the thiol and the alkaline substance; and
   (5) water for activating the mixture, and removing this composition with the necrotic tissue after leaving the composition in contact with the skin for a number of minutes.

2. The method according to claim 1, wherein the alkaline substance is selected from the group consisting of guanidine and alkali and alkaline earth metal hydroxides, carbonates, silicates, tribasic phosphates, and a mixture of any of these.

3. The method according to claim 1, wherein the alkaline substance is present in an amount of from 3 to 20 weight percent.

4. The method according to claim 2, wherein the alkaline substance is calcium hydroxide.

5. The method according to claim 1, wherein the alkaline substance is present in a sufficient amount to provide a pH of 11 to 12 in the final preparation.

6. The method according to claim 1, wherein the alkaline substance is present in an amount of from 4 to 12 percent by weight of the final preparation.

7. The method according to claim 1, wherein the substituted thiol is an alkaline earth thioglycolate, an alkali metal thioglycolate, or a mixture thereof.

8. The method according to claim 1, wherein the substituted thiol is calcium thioglycolate.

9. The method according to claim 1, wherein the application vehicle comprises (a) a body-giving material having an oily characteristic which can be emulsified with water, (b) an emulsifying material to emulsify the body-giving material, (c) a thickening material to thicken an emulsion, and (d) sufficient water to provide a consistency to the application vehicle permitting intimate contact among the thiol, allantoin, alkaline substance and necrotic tissue.

10. The method according to claim 1, wherein the composition remains in contact with the affected skin for at least 10 minutes and sometimes up to 30 minutes.

11. The method according to claim 1, wherein the composition to be applied to the effected skin comprises:
   (1) about 2 to 12 percent by weight, based on the total composition, of an alkaline earth metal thioglycolate or an alkali metal thioglycolate;
   (2) 5 to 15 percent of an alkaline earth hydroxide;
   (3) 0.5 to 5 percent allantoin;
   (4) an application vehicle for the thiol and alkaline substance;
   (5) water; and
   (6) optionally an anti-oxidant, a preservative, and a soothing agent.

12. A method for removing necrotic tissue of patients afflicted by psoriasis which comprises applying to the affected skin a composition comprising:
   (1) about 2 to 12 percent, based on the total composition, of an alkaline earth thioglycolate;
   (2) 2 to 5 percent allantoin;
   (3) 5 to 15 percent alkaline earth or alkali metal hydroxide or a combination of hydroxide and carbonate;
   (4) water;
   (5) a suitable emollient base; and
   (6) optionally one or more antioxidant, preservative, soothing agent, fragrance, and coloring agent, and removing this composition with the necrotic tissue after leaving the composition in contact with the skin for a number of minutes.

13. The method according to claim 12, wherein the composition remains in contact with the affected skin for at least 10 minutes and sometimes up to 30 minutes.

* * * * *